United States Patent [19]

Nauman

[11] Patent Number: 4,763,656
[45] Date of Patent: Aug. 16, 1988

[54] TRANSCUTANEOUS ELECTRICAL NERVE STIMULATION DEVICE AND METHOD

[75] Inventor: Edward A. Nauman, Signal Hill, Calif.

[73] Assignee: Beatrice T. Kester, Beverly Hills, Calif.

[21] Appl. No.: 134,195

[22] Filed: Dec. 17, 1987

Related U.S. Application Data

[63] Continuation-in-part of Ser. No. 744,248, Jun. 13, 1985, abandoned.

[51] Int. Cl.$^4$ .............................................. A61N 1/36
[52] U.S. Cl. ................................................. 128/421
[58] Field of Search ......... 128/419 PS, 419 E, 419 R, 128/421–423

[56] References Cited

U.S. PATENT DOCUMENTS

| | | | |
|---|---|---|---|
| 2,333,760 | 11/1943 | Babo et al. | 128/422 |
| 2,465,838 | 3/1949 | Bernard | 128/421 |
| 2,477,084 | 7/1949 | Rehman | 128/423 |
| 2,558,270 | 6/1951 | Reiter | 128/423 |
| 2,785,680 | 3/1957 | Esnault-Pelterk | 128/419 R |
| 2,936,762 | 3/1960 | Bernard | 128/422 |
| 3,646,940 | 3/1972 | Timm et al. | 128/421 |
| 3,662,758 | 5/1972 | Glover | 128/419 E |
| 3,911,930 | 10/1975 | Hagfors et al. | 128/421 |
| 3,945,387 | 3/1976 | Adams | 128/419 PG |
| 4,153,059 | 5/1979 | Fravel et al. | 128/422 |
| 4,210,151 | 7/1980 | Keller, Jr. | 128/421 |
| 4,453,548 | 6/1984 | Maurer et al. | 128/421 |

*Primary Examiner*—William E. Kamm
*Attorney, Agent, or Firm*—Bruce L. Birchard

[57] ABSTRACT

A transcutaneous nerve stimulation device and method in which trains of pulses with exponential decay-times but having fixed amplitudes, fixed widths at the time-axis and fixed repetition rates have their decay-times modulated over a series of discrete values or continuously by means of binary-counter-switched time-constant capacitors.

7 Claims, 2 Drawing Sheets

TRANSCUTANEOUS ELECTRICAL NERVE STIMULATION DEVICE AND METHOD

RELEVANT CO-PENDING APPLICATION

This application is a continuation-in-part of application Ser. No. 06/744,248 filed by the same applicant on June 13, 1985, now abandoned.

BACKGROUND OF THE INVENTION

1. Field of the Invention

This invention relates to Transcutaneous Electrical Nerve Stimulation "TENS" devices and more particularly to such devices which utilize pulses having an exponential decay curve.

2. Prior Art

The prior art includes various disclosures of transcutaneous nerve-stimulator devices in which pulse width, amplitude and repetition rate are fixed or varied. However, field tests show that stimulation signals of fixed characteristics and even those in which width, rate and/or amplitude vary suffer from ineffectiveness after a period of usage through a human neurophysical phenomenon known as "accommodation". As a result, such TENS devices fail to provide the patent with maximum relief from pain over an extended period of time.

Therefore, it is an object of this invention to overcome the disadvantages of the prior art as have been set forth herein.

It is a further object of this invention to provide a TENS device which supplies to the patient a stresm of pulses with a unique characteristic being varied so that the patent receives continuing relief over an extended period of use of the TENS device.

SUMMARY OF THE INVENTION

The subject TENS device utilizes pulses with exponential decay times but with fixed widths along the time axis. The decay-times of the pulses are modulated over a series of discrete values. By modifying the decay-times of the exponential pulses utilized in the device and method according to this invention, but keeping widths and amplitudes of the pulses, and their repetition rates, fixed, not only the amount of energy per pulse is changed but the actual characteristics of the pulses and pulse groups, as experienced by the nervous system of the patient, are changed. Thus the accommodation phenomenon experienced in other TENS devices and methods is avoided and the long term efficacious use of the TENS device and method according to this invention is enhanced. Experience with patients has taught that the variable or modulated-decay-time pulse feels better to the patient than the rectangular or spike-types of pulses used previously in TENS devices. The ultimate result is that the patient uses the TENS device and method according to this invention for a longer period of time and, with the elimination of the accommodation phenomenon, the pain relief to the patient is enhanced.

BRIEF DESCRIPTION OF THE DRAWINGS

This invention can best be understood by reviewing the description which follows in conjunction with the drawings herein, in which.

BRIEF DESCRIPTION OF THE PREFERRED EMBODIMENT

Figure 1:
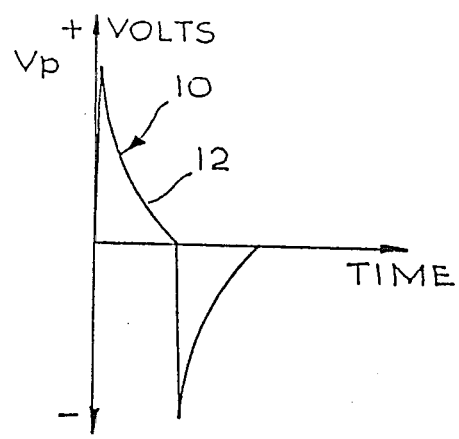
FIG. 1 is a graphical representation of a pulse of the type utilized in the present invention.

In FIG. 1, symmetrical bipolar pulse 10 has an exponential decayr egion 12 which can be defined, mathematically, by the following equation.

$$V_d(V_p)e^{-t/T}$$

WHERE:
- $V_d$ = The instantaneous voltage on the decaying curve (volts).
- $V_p$ = The maximum peak amplitude of the pulse (volts).
- $e$ = The inverse natural logarithm.
- $t$ = The time measured from peak value occurrence (seconds).
- $T$ = The time constant (seconds).

While the use of a pulse with an exponential decay is nothing new in TENS devices, this invention teaches a method of modulating the time constant, T, to produce a wave form that appears to reduce the phenomenon of accommodation in the patient utilizing the TENS device.

In the decay-time modulation mode taught by this invention, the TENS device generates a continuous stream of pulses with the decay-times of successive pulses or successive sets of pulses being modulated over, for example, eight discrete values.

Figure 2:
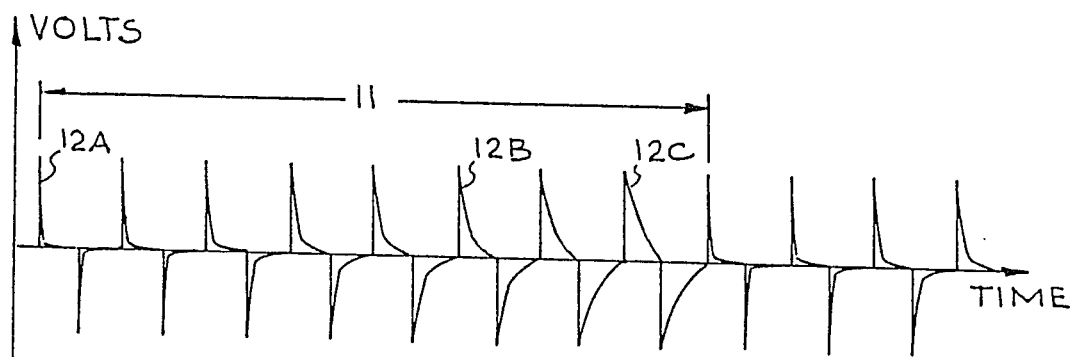
FIG. 2 is a graphical representation of a series of pulses of the type of FIG. 1 with certain characteristics varied according to the present invention.

The nature of such a wave train can be seen more clearly in FIG. 2. In FIG. 2, the decay-time starts at its maximum slope 12A, which indicates a short time constant, and is successively increased, in this example 7 times, thru exponential decay curve 12B to the final exponential curve 12C in the wave train 11, curve 12C representing the maximum time constant T utilized in this invention. The circuit then reverts to the minimum decay-time, automatically and without interruption, the the pulse train 11 is repeated.

The decay-time modulation according to this invention may have a selectively variable rate of modulation, for example, three distinct rates of modulation. Of course, the rate of modulation can be made continuously variable as well as discretely variable. The rate of modulation is determined by the number of pulses of a given decay-time that are produced and appear in the wave train before the decay-time is increased to its next value.

Figure 3:
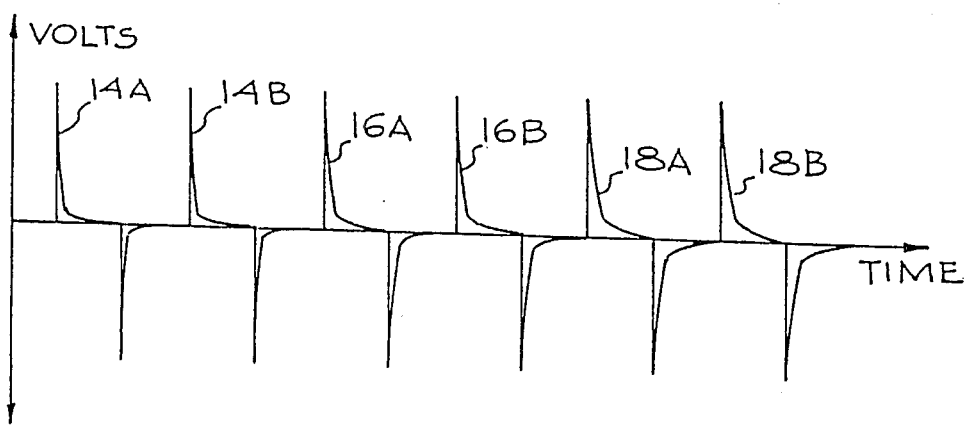
FIG. 3 is a graphical representation of a particular grouping of pulses of the type shown in FIG. 2; and, FIG. 4 is a block diagram of a TENS device according to the present invention.

In FIG. 3, there is represented the wave train according to this invention under the condition of the fastest decay-time modulation where only two pulses, 14A, 14B; 16A, 16B; and 18A, 18B, for example, are produced before the decay-time is increased to its ext value. In a device as actually built utilizing this invention the slowest rate of decay-time modulation utilized produced either pulses of each decay-time time constant. The medium rate utilized produced four of each such decay-times.

As has been noted earlier, herein, changing the width of a rectangular pulse is not the same as changing the shape of an exponential pulse. By changing the width of the rectangular pulse all that changes is the amount of energy contained in the pulse. By changing the decay-time characteristic of an exponential pulse, not only the amount of energy per pulse changes, but the actual effects of the pulse are changed. The circuit by which decay-time modulation is achieved according to the present invention is set forth in FIG. 4.

Figure 4:
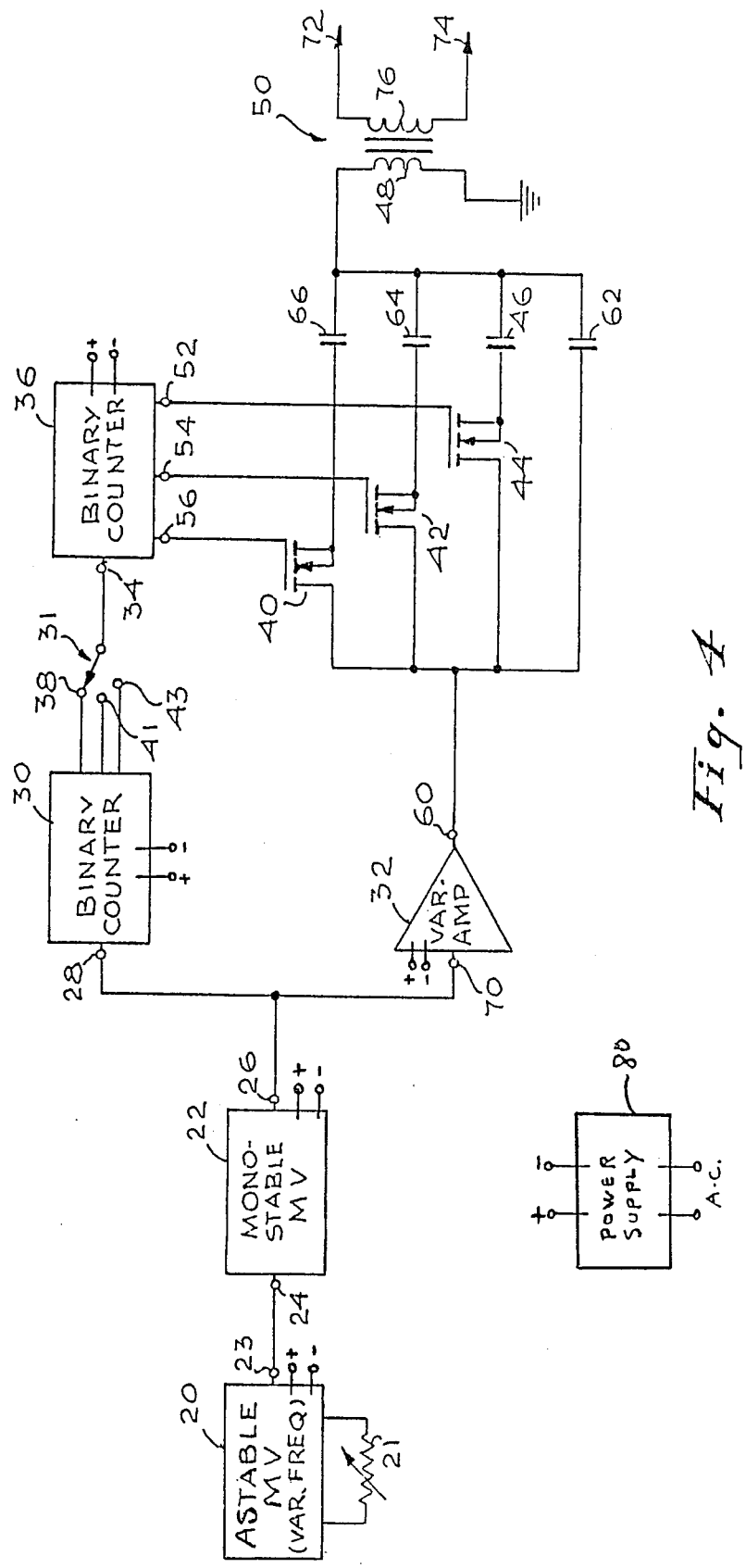

In FIG. 4, a variable-frequency astable multivibrator 20 generates a continuos rectangular pulse train with an approximate duty cycle of 50%. The frequency is variable over an approximate range of 20 Hz to 100 Hz depending on the setting of potentiometer 21. The circuit diagram are for an astable multivibrator is well known to one skilled in the art and can be found in the National Semiconductor Linear Book. Further, a microchip carrying the semiconductor elements of an astable multivibrator is provided as integrated circuit LM556 CP available from National Semiconductor. The rectangular pulse train appearing at terminal 23 of astable multivibrator 20 is applied to input terminal 24 of monostable multivibrator 22 and acts as a trigger for that multivibrator. This monostable multivibrator 22 generates a 5 millisecond pulse every time it is triggered by the astable multivibrator 20. As a result, there appears at output terminal 26 of monostable multivibrator 22 a train of rectangular pulses having a width of 5 milliseconds and having the same frequency as the frequency chosen for the astable multivibrator 20. The circuit for a monostable multivibrator is well known to one skilled in the art and need not be described here. Again, the integrated circuit chip LM556 CP may be utilized to provide the semiconductor components not only of the astable multivibrator but of the monostable multivibrator 22. One possible circuit configuration is set forth in U.S. Pat. No. 4,431,000 at FIG. 3.

The output signal from monostable multivibrator 22 as it appears at terminal 26 is applied to input terminal 28 of binary counter 30 and to the variable amplifier 32, the circuit for which is well known in the art.

1 nary counter 30 is coupled thru selector switch 31 to the input terminal 34 of a second binary counter 36. The input to selector switch 31 comes, selectively, from terminal 38, 41 or 43 of binary counter 30. Binary counter 30 acts as a frequency divider. Switch 31 is a "rate" switch and depending on whether the switch 31 is in connection with terminal 38, 41 or 43, respectively, the frequency of the pulses that reach input terminal 34 of second binary counter 36 will be either $\frac{1}{2}$, $\frac{1}{4}$, or $\frac{1}{8}$ of the frequency of the astable multivibrator 20. For example, if switch 31 is turned so that it connects with terminal 38 of first binary counter 30, binary counter 36 will count in binary fashion at half the rate of the astable multivibrator 20. In other words, it would take two pulses from the monostable multivibrator 22 to cause binary counter 36 to increment by one count.

Hexfet switches 40, 42 and 44 are electronic switches and are controlled by the output signals from second binary counter 36. For example, switch 44 is controlled by the least significant bit output of second binary counter 36. When the least significant bit is in its "on" state, switch 44 is closed allowing pulses to pass from amplitude control element 32 thru capacitor 46 to the primary winding 48 of output transformer 50.

When all three swithces, 40, 42 and 44 are open, i.e. all three output terminals 52, 54, 56 of second binary counter 36 show a zero output, the pulses derived from output terminal 60 of variable amplifier 32 reach the primary winding 48 of output transformer 50 thru capacitor 62, only. The pulses thus reaching output transformer 50 have their decay-times determined by capacitor 62 and the impedance of the patient reflected through output transformer 50. The time constant, T, is proportional to the capacitance of capacitor 62 and the reflected impedance in the primary winding 48 of output transformer 50. To increase the time constant, T, is proportional to the capacitance of capacitor 62 and the reflected impedance in the primary winding 48 of output transformer 50. To incrase the time constant, and, hence, reduce the slope of the decay curve, the time constant should be increased. This is achieved in the circuit of FIG. 4 by the switching "on" of switch 44 by a "one" signal appearing at terminal 52 of second binary counter 36.

Since second binary counter 36 counts in binary fashion and there are three bits, there are eight possible combinations of states of switches 40, 42 and 44 ranging from all "off" to all "on". The values of capacitance of capacitors 62, 64 and 66 are binarily weighted as closely as possible by using standard values. The net effect of this combination, is to increase the time constant by approximately an equal amount every time that second binary counter 36 increments. When second binary counter 36 counts to its limit it resets and resumes counting.

The circuit of FIG. 4 operates as follows. With switch 31 set in the position shown in FIG. 4, it takes two pulses from monostable multivibrator 22 to increment second binary counter 36. This is the fastest setting of the decay-time modulation system described in connection with this invention. If we start with all of the switches 40, 42 and 44 "on" (that is, with all outputs of second binary counter 36 "high") the next pulse applied to input terminal 34 of second binary counter 36 will increment second binary counter 36 and turn all of the switches 40, 42 and 44 to an "off" state. At the same time, that pulse wll pass thru the variable amplifier 32 by way of input terminal 70 and output terminal 60, thru capacitor 62 and into the primary winding 48 of transformer 50 to produce at output terminals 72, 74 a pulse with the minimum decay-time for this system. The next pulse applied to input terminal 34 of second binary counter 36 also passes thru capacitor 62, only, on its way to primary winding 48 of transformer 50 with a resulting output pulse at terminal 72 and 74 which is the same, as far as decay-time is concerned, as the first pulse, just discussed. This situation arises because of the fact that it takes two pulses applied to input terminal 34 of second binary counter 36 to cause binary counter 36 to increment.

The third pulse applied to input terminal 34 of second binary counter 36 causes that second binary counter to increment by producing a "high" at terminal 52 and turns on switch 44. With switch 44 turned "on" the third pulse now passes thru capacitors 62 and 46. The resulting output pulse at terminals 72 and 74 of output transformer 50 shows a lower slope in the decay curve than the previous pulse which involved only capacitor 62. The fourth pulse applied to input terminal 34 of second binary counter 36 also passes thru capacitors 62 and 46, only, because of the two pulses required by second binary counter 36 to produce at incrementing of that counter.

The fifth pulse applied to input terminal 34 of second binary counter 36 causes that second binary counter 36 to increment, producing a "high" on output terminal 54 and a zero on output terminal 52. As a result, switch 44 is turned "off" and switch 42 is turned "on". The result of this circuit combination is that the fifth and sixth pulses applied to input terminal 34 of second binary counter 36 now pass thru capacitors 62 and 64. The output pulse appearing at terminals 72 and 74 of output transformer 50 has a different decay-time characteristic as a result a of the change in the capacitance values since capacitor 46 has now been switched out and capacitor 64 has been switched in.

The seventh pulse applied to input terminal 34 of second binary counter 36 causes it to increment, which turns on switch 44, again, causing pulses 7 and 8 applied to input terminal 34 of binary counter 36 to pass thru capactiors 62, 46 and 64, increasing the time constant of the decay-curve and broadening the pulse which appears between terminals 72 and 74 of output winding 76 on output transformer 50. The next pulse, pulse 9, applied to input terminal 34 of second binary counter 36 increments that counter which results in turning off switches 42 and 44 and turning on switch 40. Therefore, pulses 9 and 10 applied to input terminal 34 of binary counter 36 now pass thru capacitors 62 and 66, again varying the time constant in the output circuit and causing the decay-curve to be changed in its slope.

The eleventh pulse applied to input terminal 34 of second binary counter 36 causes that counter to increment turning switch 44 "on". As a result, pulses 11 and 12 pass thru capacitors 62, 46 and 66. The decay-curve of the pulse appearing at output terminal 72 and 74 of output winding 76 in transformer 50 is again changed over that which it was previously.

When pulse 13 arrives at input terminal 34 of second binary counter 36 it increments that counter turning switch 44 "off" and switch 42 "on". Pulses 13 and 14 then pass thru capacitors 62, 64 and 66 before being applied to primary 48 of output transformer 50. Once again the decay-curve of the pulse appearing across terminals 72 and 74 of output winding 76 is changed from the next previous condition.

Pulse 15 arriving at input terminal 34 of second binary counter 36 causes that counter to increment turning switch 44 "on". Pulses 15 and 16 appearing at input terminal 34 of second binary counter 36 now pass thru all four capacitors 62, 46, 64 and 66. The pulses appearing across terminals 72 and 74 of output winding 76 have the lowest slope, i.e., the time constant is longest, as compared with any of the previous pulses appearing across output terminals 72, 74.

The next pulse, pulse 17 appearing at input terminal 34 of second binary counter 36 is the new pulse No. 1 and it causes second binary counter 36 to increment turning off all three switches 40, 42 and 44 and restarting the entire sequence. Thus decay-time modulation is achieved in the circuit of FIG. 4.

While, for simplification purposes, FIG. 2 shows only one pulse of each decay-time paramemter being produced before the decay-time is increased to its next value, it should be understood that the graph of FIG. 2 is for illustrational purposes only. As has been stated, in the fast mode of decay-time modulation there are two pulses of each decay-time paramemter produced before the next decay-time parameter is established. Similarly, there are four pulses of each decay-time parameter produced in the medium rate and eight produced in the slow rate before the next decay-time parameter pulses are produced. The matter of whether two, four or eight pulses are included in each decay-time parameter group is determined by the setting of switch 31. Of course, operating power for the various elements of the device may be provided by a power supply, such as power supply 80.

While a particular embodiment of this invention has been shown and described, it is apparent to those ordinarily skilled in the art that alterations and/or modifications may be made therein without departing from the true scope of this invention. It is the purpose of the appended claims to cover all such alterations and modifications.

I claim:

1. A transcutaneous nerve stimulation device including:
    generating means for generating a train of electrical pulses of fixed time-axis width and having decay-tubes;
    modulating means coupled to said generating means for modulating the decay-times of said electrical pulses of fixed time-axis width within said train;
    means electrically coupled to said generating and modulation means for providing electrical operating power thereto; and,
    electrical pulse output terminals electrically coupled to said generating means for applying decay-time-modulated electrical pulses of fixed time-axis width therefrom to a patient.

2. Apparatus according to claim 1 in which said modulating means includes means for selecting the rate of modulation of said decay-times.

3. Apparatus according to claim 1 in which said modulating means includes binary-counting means, switching means transformer coupled to said binary-counting means and controlled thereby and time-constant capactior means coupled between said switching means and said electrical pulse output terminals and controlled by said switching means.

4. Apparatus according to claim 3 in which said switching means includes at least one FET switch controlled by said binary-counting means.

5. The method of operating a transcutaneous nerve stimulation device which includes the steps of generating train of pulses having fixed widths along the time-axis and having decay-times, modulating the decay-times within said train of pulses having fixed widths along the time-axis and applying the pulses to a patient.

6. The method according to claim 5 which includes the additional step of automatically changing the modulation rate.

7. A transcutaneous nerve stimulation device including:
    generating means for generating a train of electrical pulses of fixed time-axis width and repetition rate and having decay-times;
    modulating means coupled ; to said generating means for modulating the decay-times of said electrical pulses of fixed time-axis width and repetition rate within said train;
    electrical pulse output terminals electrically coupled to said generating means for deriving decay-time-modulated electrical pulses of fixed time-axis width and repetition rate therefrom to apply to a patient; and,
    means for supplying operating power to the device.

* * * * *